(12) United States Patent
Heraty et al.

(10) Patent No.: US 9,539,120 B2
(45) Date of Patent: Jan. 10, 2017

(54) MEDICAL DEVICE SUITABLE FOR LOCATION IN A BODY LUMEN

(75) Inventors: Kevin Heraty, Castlebar (IE); Liam Mullins, Athlone (IE); Paul Gilson, Moycullen (IE); Martin Burke, Tuam (IE)

(73) Assignee: Veryan Medical Ltd., Horsham (GB)

( * ) Notice: Subject to any disclaimer, the term of this patent is extended or adjusted under 35 U.S.C. 154(b) by 0 days.

(21) Appl. No.: 12/249,424

(22) Filed: Oct. 10, 2008

(65) Prior Publication Data

US 2010/0094402 A1   Apr. 15, 2010

(51) Int. Cl.
*A61F 2/82* (2013.01)
*A61F 2/30* (2006.01)

(52) U.S. Cl.
CPC ............... *A61F 2/82* (2013.01); *A61F 2/3094* (2013.01); *A61F 2002/30019* (2013.01); *A61F 2002/30199* (2013.01); *A61F 2230/0063* (2013.01); *A61F 2240/001* (2013.01); *A61F 2250/0006* (2013.01); *A61F 2250/0029* (2013.01); *A61F 2250/0048* (2013.01)

(58) Field of Classification Search
CPC ............... A61F 2/06; A61F 2/07; A61F 2/82; A61F 2250/0048; A61F 2250/0029; A61F 2250/0006
USPC ....................... 623/1.1, 1.15, 1.22, 1.34, 1.18
See application file for complete search history.

(56) References Cited

U.S. PATENT DOCUMENTS

| | | | |
|---|---|---|---|
| 5,449,373 A | 9/1995 | Pinchasik et al. | |
| 5,938,697 A | 8/1999 | Killion et al. | |
| 6,270,524 B1 | 8/2001 | Kim | |
| 6,896,697 B1 | 5/2005 | Yip et al. | |
| 7,018,401 B1 | 3/2006 | Hyodoh et al. | |
| 7,625,400 B2 * | 12/2009 | Bowe | A61F 2/91 623/1.11 |
| 7,731,747 B2 | 6/2010 | Kaplan et al. | |
| 8,226,704 B2 * | 7/2012 | Caro | A61F 2/07 623/1.17 |

(Continued)

FOREIGN PATENT DOCUMENTS

| | | |
|---|---|---|
| EP | 0 800 801 A1 | 10/1997 |
| EP | 0 951 877 | 10/1999 |

(Continued)

OTHER PUBLICATIONS

European Search Report corresponding to EP 08 25 3319, Jan. 15, 2009 (English Text).

(Continued)

*Primary Examiner* — Christian Sevilla
*Assistant Examiner* — Seema Mathew
(74) *Attorney, Agent, or Firm* — Fay Sharpe LLP

(57) ABSTRACT

A stent (1) for deployment in a blood vessel which is movable between an unloaded straight cylindrical state and a loaded curved state. The stent (1) is bendable between a first loaded configuration when the blood vessel is in the unloaded state, and a second loaded configuration when the blood vessel is in the loaded state. The stent (1) has an unloaded configuration which is intermediate the first loaded configuration and the second loaded configuration. Because of the unloaded configuration of the stent (1), the degrees of deformation which the stent (1) undergoes are minimized leading to minimized strains, increased fatigue life, and reduced risk of fracture.

15 Claims, 5 Drawing Sheets

(56) References Cited

U.S. PATENT DOCUMENTS

| | | | | |
|---|---|---|---|---|
| 8,425,585 | B2* | 4/2013 | Melsheimer | A61F 2/07 623/1.13 |
| 8,882,826 | B2* | 11/2014 | Ta | A61F 2/91 623/1.16 |
| 2001/0025130 | A1* | 9/2001 | Tomonto | A61F 2/91 600/36 |
| 2002/0179166 | A1 | 12/2002 | Houston et al. | |
| 2002/0183853 | A1 | 12/2002 | Mitchell et al. | |
| 2003/0088305 | A1* | 5/2003 | Van Schie | A61F 2/06 623/1.12 |
| 2003/0187497 | A1 | 10/2003 | Boylan et al. | |
| 2005/0096733 | A1 | 5/2005 | Kovneristy et al. | |
| 2006/0030926 | A1* | 2/2006 | Berra | A61F 2/06 623/1.13 |
| 2006/0217795 | A1 | 9/2006 | Besselink et al. | |
| 2006/0265051 | A1* | 11/2006 | Caro | A61F 2/07 623/1.17 |
| 2007/0055299 | A1* | 3/2007 | Ishimaru | A61F 2/07 606/191 |
| 2008/0086854 | A1 | 4/2008 | Boyd et al. | |
| 2008/0262599 | A1* | 10/2008 | Caro | A61F 2/82 623/1.16 |
| 2008/0306440 | A1* | 12/2008 | Hirszowicz | A61M 25/1002 604/99.01 |
| 2009/0149945 | A1 | 6/2009 | Pike | |
| 2009/0234431 | A1* | 9/2009 | Weinberger | A61F 2/06 623/1.13 |
| 2010/0094403 | A1* | 4/2010 | Heraty | A61F 2/958 623/1.15 |
| 2010/0286759 | A1* | 11/2010 | Taylor | A61F 2/82 623/1.15 |
| 2012/0283819 | A1* | 11/2012 | Taylor | A61F 2/82 623/1.22 |
| 2012/0330402 | A1* | 12/2012 | Vad | A61F 2/07 623/1.13 |

FOREIGN PATENT DOCUMENTS

| | | |
|---|---|---|
| EP | 1 279 382 A1 | 1/2003 |
| EP | 2 174 623 A1 | 4/2010 |
| EP | 2 174 624 A1 | 4/2010 |
| GB | 2 418 362 A | 3/2006 |
| GB | 2 425 485 | 11/2006 |
| JP | H 11-332998 | 12/1999 |
| JP | 2005-013302 | 1/2005 |
| JP | 2008-513171 | 5/2008 |
| WO | WO 98/20810 | 5/1998 |
| WO | WO 03/059199 A1 | 7/2003 |
| WO | WO 2006/032902 | 3/2006 |
| WO | WO 2007/053791 A1 | 5/2007 |
| WO | WO 2007/062661 A1 | 6/2007 |
| WO | WO 2008/125842 A1 | 10/2008 |
| WO | WO 2010128311 A1 * 11/2010 ............... A61F 2/82 |

OTHER PUBLICATIONS

International Search Report of International Application No. PCT/GB2009/002434 dated Jan. 19, 2010 (English Text).

* cited by examiner

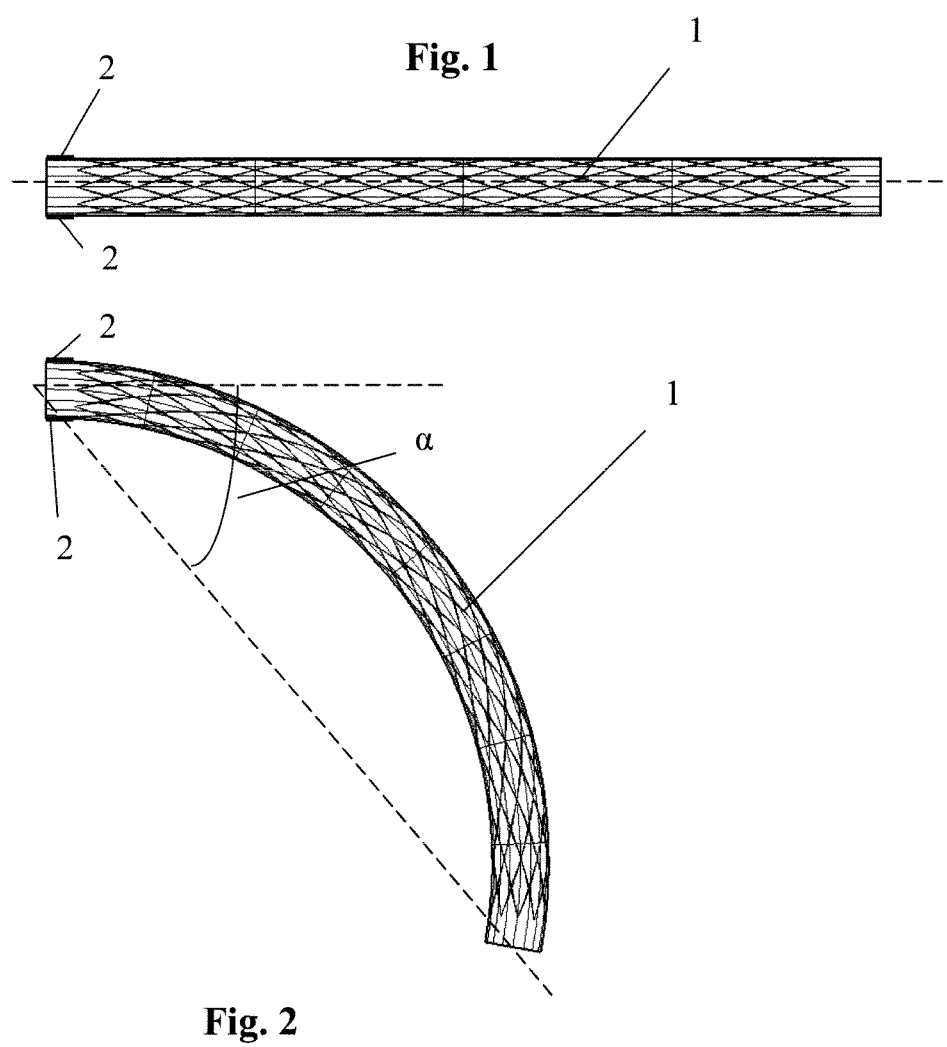

Fig. 4
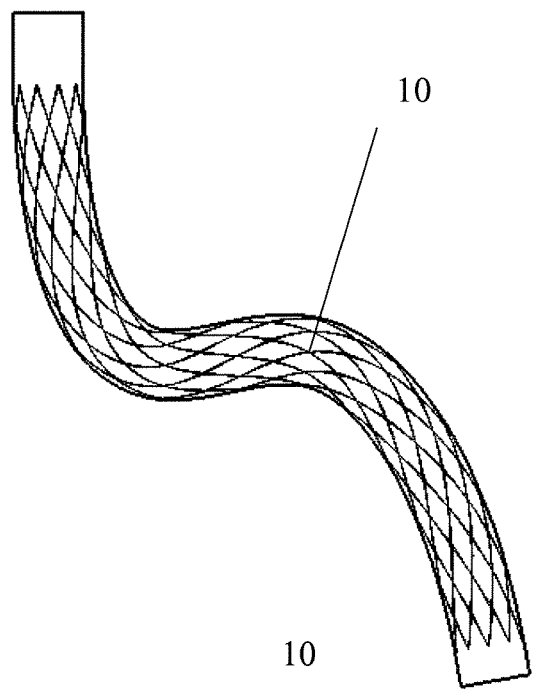
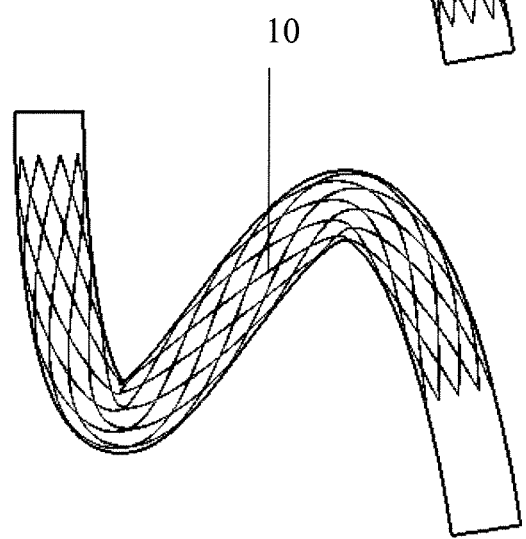
Fig. 5

Fig. 7
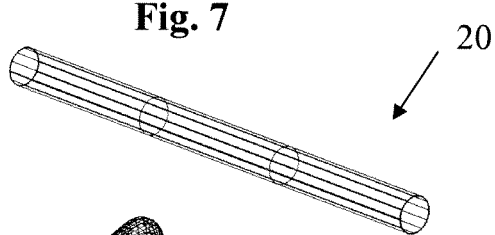
20
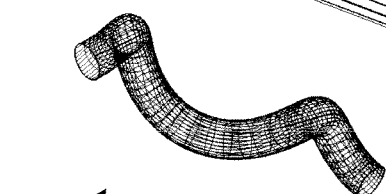
20
Fig. 8
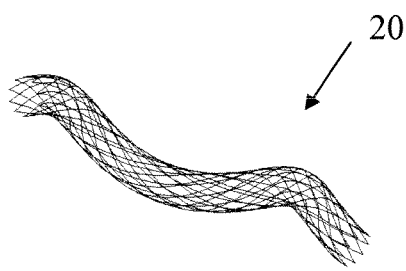
20
Fig. 9

MEDICAL DEVICE SUITABLE FOR LOCATION IN A BODY LUMEN

INTRODUCTION

This invention relates to a medical device suitable for location in a body lumen.

STATEMENTS OF INVENTION

According to the invention there is provided a medical device suitable for location in a body lumen, the device being movable between a first loaded configuration and a second loaded configuration, the device having an unloaded configuration intermediate the first loaded configuration and the second loaded configuration. The degree of deformation which the device undergoes moving from the unloaded configuration to either the first loaded configuration or the second loaded configuration is less than the device would undergo moving directly from the first loaded configuration to the second loaded configuration.

In one embodiment of the invention the device is suitable for location in a body lumen which is movable between an unloaded state and a loaded state. Preferably the device is configured to be in the first loaded configuration when a body lumen is in an unloaded state. Ideally the device is configured to be in the second loaded configuration when a body lumen is in a loaded state.

The device may be deformable between the first loaded configuration and the second loaded configuration. In one case the device is bendable between the first loaded configuration and the second loaded configuration. The device may be twistable between the first loaded configuration and the second loaded configuration. The device may be compressible between the first loaded configuration and the second loaded configuration. In the unloaded configuration at least part of the longitudinal axis of the device may be curved in a two-dimensional plane. In the unloaded configuration at least part of the longitudinal axis of the device may be curved in three-dimensional space. Preferably in the unloaded configuration at least part of the device is substantially helically shaped, for example the longitudinal axis of that part may be substantially helical.

The unloaded configuration may be approximately midway between the first loaded configuration and the second loaded configuration.

The device may comprise means to align the device relative to a body lumen. Preferably the alignment means comprises means to visualise the device. Ideally the alignment means comprises one or more markers on the device. The alignment means is preferably rotational alignment means. For example, in the case of a curved device (whether curved in a two-dimension plane or in a three-dimensional space), the provision of rotational alignment means enables the curvature of the device to be generally aligned with the curvature of a body lumen.

The device may be suitable for location in a blood vessel. Preferably the device comprises a stent suitable for deployment in a blood vessel.

In one case the invention provides a stent with geometry optimised for vessel deformation.

Viewed from another aspect, the invention provides a method of treating a body lumen, comprising locating in the body lumen a device which is movable between a first loaded configuration and a second loaded configuration, the device having an unloaded configuration intermediate the first loaded configuration and the second loaded configuration. The device may be located in a body lumen which is movable between an unloaded state and a loaded state. The device may be configured to be in the first loaded configuration when a body lumen is in an unloaded state. The device may be configured to be in the second loaded configuration when a body lumen is in a loaded state.

In a preferred method, the device is a stent and the method comprises locating the stent in a blood vessel behind a knee of a patient.

BRIEF DESCRIPTION OF THE DRAWINGS

The invention will be more clearly understood from the following description of some embodiments thereof, given by way of example only, with reference to the accompanying drawings, in which:

FIG. 1 is a side view of a medical device according to the invention in a first loaded configuration located in a body lumen;

FIG. 2 is a side view of the device of FIG. 1 in a second loaded configuration located in the body lumen;

FIG. 4 is a side view of another medical device according to the invention in a first loaded configuration located in a body lumen;

FIG. 5 is a side view of the device of FIG. 4 in a second loaded configuration located in the body lumen;

FIG. 7 is an isometric view of another medical device according to the invention in a first loaded configuration;

FIG. 8 is an isometric view of the device of FIG. 7 in a second loaded configuration; and FIG. 9 is an isometric view of the device of FIG. 7 in an unloaded configuration.

DETAILED DESCRIPTION

Figure 3:
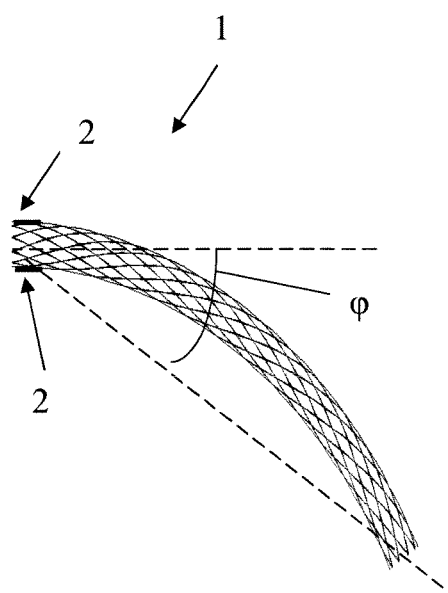
FIG. 3 is a side view of the device of FIG. 1 in an unloaded configuration.

Referring to the drawings, and initially to FIGS. 1 to 3 thereof, there is illustrated a medical device 1 according to the invention suitable for location in a body lumen. The medical device 1 is movable between a first loaded configuration (FIG. 1) and a second loaded configuration (FIG. 2).

In this case the medical device 1 comprises a stent suitable for deployment in a blood vessel which is movable between an unloaded straight cylindrical state (FIG. 1) and a loaded curved state (FIG. 2). The stent 1 supports at least part of an internal wall of the blood vessel. The stent 1 is in the first loaded configuration when the blood vessel is in the unloaded state (FIG. 1), and the stent 1 is in the second loaded configuration when the blood vessel is in the loaded state (FIG. 2).

The stent 1 is bendable through a single bend between the first loaded configuration (FIG. 1) and the second loaded configuration (FIG. 2).

The stent 1 has an unloaded configuration (FIG. 3) which is intermediate the first loaded configuration and the second loaded configuration. In the unloaded configuration the stent 1 is in a rest state. In this case the unloaded configuration is approximately midway between the first loaded configuration and the second loaded configuration. In the unloaded configuration the longitudinal axis of the stent 1 is curved through a single bend in a two-dimensional plane.

In this case no shape change occurs upon delivery of the stent 1 to the blood vessel. The stent 1 has the same unloaded configuration outside of the blood vessel prior to delivery and after deployment in the blood vessel.

The stent 1 may be balloon expandable or self-expanding.

The stent 1 is suitable for use in the blood vessel which is subject to tortuous loading, such as bending. The stent 1 has the pre-set curved geometry in the unloaded configuration, as shown in FIG. 3. The choice of pre-set curve is determined by the extremes of deformation which occur in the blood vessel in which the stent 1 will be implanted. The unloaded configuration of the stent 1 represents a configuration between two opposing extremes of deformation of the blood vessel, such as those shown in FIGS. 1 and 2.

Because of physiological movements within the body, the blood vessel may be forced to adopt tortuous configurations. Large degrees of bending may occur, for example with bends in excess of 90°. The location for the stent 1 may be in the blood vessel in the leg behind the knee which is subject to frequent bending as the patient bends the leg. Because the unloaded configuration of the stent 1 is non-straight, the degrees of deformation which the stent 1 undergoes are minimised leading to minimised strains, increased fatigue life, and reduced risk of fracture.

The configuration of FIGS. 1 to 3 results in the stent 1 bending by a maximum of $\phi$ degrees, that is from $\phi$ degrees to 0 degrees (FIG. 3 to FIG. 1), or from $\phi$ degrees to $\alpha$ degrees (FIG. 3 to FIG. 2). In this case $\alpha=2\phi$. This contrasts with the conventional approach of bending a stent by $\alpha$ degrees each time, that is from 0 degrees to $\alpha$ degrees (FIG. 1 to FIG. 2).

FIGS. 1 to 3 illustrate a single bend in one plane. FIG. 1 illustrates the stent 1 deployed in the unloaded vessel, FIG. 2 illustrates the stent 1 deployed in the loaded vessel, and FIG. 3 illustrates the stent 1 in the unloaded configuration.

Since some of the deformation of the blood vessel is already incorporated in the stent 1 in the unloaded configuration (FIG. 3), the strains induced through further deformation of the stent 1 to achieve the fully loaded configuration (FIG. 2) are less than those which would be induced if the stent 1 had to go from the straight (FIG. 1) to the fully loaded configuration of the blood vessel (FIG. 2).

For example, as shown in FIGS. 1 to 3, in a blood vessel which bends between 0 degrees and $\alpha$ degrees in one plane, the curved stent 1 in the unloaded configuration already accommodates the angle of $\phi$ degrees. Therefore in order to bend from 0 degrees to $\alpha$ degrees, the stent 1 bends from $(-\phi)$ degrees to $(\alpha-\phi)$ degrees. Improved mechanical performance is achieved since the induced strains at angles of $(-\phi)$ degrees and $(\alpha-\phi)$ degrees are less than those induced by bending a straight stent from 0 degrees to $\alpha$ degrees.

The stent 1 comprises visualisation means to align the stent 1 relative to the blood vessel. In this case the alignment means comprises one or more markers 2 on the stent 1. A pair of markers 2 are provided in this embodiment, both at one end of the stent 1 and positioned diametrically opposite each other. The stent 1 may be oriented at the implantation site, for example using the radiopaque markers or other visualisation means. The rotational position of the stent may be adjusted during implantation whilst using the markers to visualise the rotational position. The stent 1 may be aligned with the axis of bending of the knee of a patient during deployment.

In use, the stent 1 is delivered into the blood vessel and deployed at a desired treatment site in the blood vessel. The stent 1 may be oriented at the desired treatment site.

As the blood vessel moves from the unloaded straight cylindrical state (FIG. 1) to the loaded curved state (FIG. 2), the stent 1 bends from the first loaded configuration to the second loaded configuration.

Figure 6:
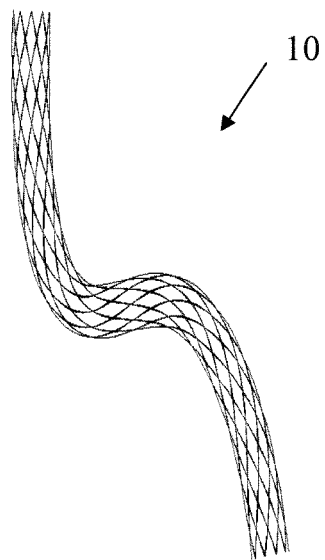
FIG. 6 is a side view of the device of FIG. 4 in an unloaded configuration.

In FIGS. 4 to 6 there is illustrated another medical device 10 according to the invention, which is similar to the medical device 1 of FIGS. 1 to 3.

In this case the stent 10 is bendable through two bends between the first loaded configuration (FIG. 4) and the second loaded configuration (FIG. 5).

In the unloaded configuration the longitudinal axis of the stent 10 is curved through two bends in a two-dimensional plane (FIG. 6).

FIGS. 4 to 6 illustrate multiple bends in one plane. FIG. 4 illustrates the stent 10 deployed in the unloaded vessel, FIG. 5 illustrates the stent 10 deployed in the loaded vessel, and FIG. 6 illustrates the stent 10 in the unloaded configuration.

The curve embodied represents a configuration between the two opposing extremes of deformation of the blood vessel, such as those shown in FIGS. 4 and 5. In this case, the stent geometry, as shown in FIG. 6, represents a deformed state in between the straight unloaded state (FIG. 4) and the loaded state (FIG. 5).

FIGS. 7 to 9 illustrate a further medical device 20 according to the invention, which is similar to the medical device 1 of FIGS. 1 to 3.

In this case the stent 20 is bendable and twistable through multiple bends between the first loaded configuration (FIG. 7) and the second loaded configuration (FIG. 8).

In the unloaded configuration the longitudinal axis of the stent 20 is curved through multiple bends in three-dimensional space (FIG. 9). In this case in the unloaded configuration the stent 20 is helically shaped.

When the stent 20 is deployed in the blood vessel, the stent 20 exerts force on the blood vessel causing the blood vessel to adopt a helical configuration. In this manner the stent 20 acts to support at least part of the internal wall of the blood vessel in the helical configuration. Blood flowing through the helically shaped blood vessel then undergoes a swirling action. The swirling flow of blood has been found to minimise thrombosis and platelet adhesion, and to minimise or prevent coverage of the stent 20 by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

FIGS. 7 to 9 illustrate multiple bends of the blood vessel in two planes allowing the stent 20 to shorten in a controlled fashion and under lower strains. FIG. 7 illustrates the unloaded vessel, FIG. 8 illustrates the loaded vessel, and FIG. 9 illustrates the stent 20 in the unloaded configuration.

It will be appreciated that the stent may be moved between the first loaded configuration and the second loaded configuration under the action of any loading mode. For example the device may be deformed between the first loaded configuration and the second loaded configuration, and/or the device may be compressed between the first loaded configuration and the second loaded configuration.

The invention is not limited to the embodiments hereinbefore described, with reference to the accompanying drawings, which may be varied in construction and detail.

The invention claimed is:
1. A method of stenting a body lumen comprising:
    deploying a stent in a body lumen;

expanding the stent to a fully expanded deployed configuration in the body lumen such that the stent is ready for use, wherein in this fully expanded deployed configuration the stent can have a first loaded configuration, a second loaded configuration and an unloaded configuration intermediate the first and second loaded configurations, the unloaded configuration being one in which at least part of the longitudinal axis of the stent is curved to a first curved state; and after the step of expanding the stent to the fully expanded deployed configuration, carrying out the following subsequent steps:

deforming the stent to the first loaded configuration when the body lumen bends to an unloaded state thereof; and deforming the stent from the first loaded configuration through the unloaded configuration to the second loaded configuration when the body lumen bends to a loaded state thereof which is more curved than said unloaded state of the body lumen;

wherein the first loaded configuration of the stent is one in which the at least part of the longitudinal axis of the stent is less curved than in the first curved state of the unloaded configuration of the stent; and wherein the second loaded configuration of the stent is one in which the at least part of the longitudinal axis of the stent is more curved than in the first curved state of the unloaded configuration of the stent.

2. A method as claimed in claim 1 wherein in the unloaded configuration at least part of the longitudinal axis of the stent is curved in a two-dimensional plane.

3. A method as claimed in claim 1 wherein in the unloaded configuration at least part of the longitudinal axis of the stent is curved in three-dimensional space.

4. A method as claimed in claim 3 wherein in the unloaded configuration at least part of the stent is substantially helically shaped.

5. The method of claim 4 further comprising:
exerting a force on the body lumen with the stent; and
causing the body lumen to adopt a helical configuration.

6. The method of claim 5 wherein an amplitude of a helical longitudinal axis of the stent divided by a diameter of the stent is greater in the second loaded configuration than in the unloaded configuration.

7. A method as claimed in claim 1 wherein the unloaded configuration is approximately midway between the first loaded configuration and the second loaded configuration.

8. A method as claimed in claim 1 wherein the stent is suitable for location in a blood vessel.

9. The method of claim 1 wherein the step of moving includes deforming the stent between the first loaded configuration and the second loaded configuration.

10. A method of claim 9 wherein the step of deforming includes twisting the stent between the first loaded configuration and the second loaded configuration.

11. The method of claim 9 wherein the step of deforming includes bending the stent between the first loaded configuration and the second loaded configuration.

12. The method of claim 9 wherein the step of deforming includes compressing the stent between the first loaded configuration and the second loaded configuration.

13. The method of claim 1 further comprising aligning the stent relative to the body lumen.

14. The method of claim 13 wherein aligning the stent includes locating at least one marker on the stent.

15. The method of claim 13 further comprising visualizing the stent relative to the body lumen.

* * * * *